United States Patent [19]

Sherwin et al.

[11] 4,012,424

[45] Mar. 15, 1977

[54] CRACKING OF MIXTURES CONTAINING HYDROXYESTERS

[75] Inventors: Martin B. Sherwin, Wayne, N.J.; Jimmy Peress, West Haven, Conn.

[73] Assignee: Chem Systems Inc., New York, N.Y.

[22] Filed: Aug. 7, 1975

[21] Appl. No.: 602,738

[52] U.S. Cl. .................. 260/348 R; 260/488 F
[51] Int. Cl.$^2$ ...................... C07D 301/02
[58] Field of Search .................. 260/348 R

[56] References Cited

UNITED STATES PATENTS 3,789,065  1/1974  Kollar .................. 260/497 R

FOREIGN PATENTS OR APPLICATIONS 812,109  9/1974  Belgium
1,124,862  8/1968  United Kingdom Primary Examiner—Norma S. Milestone
Attorney, Agent, or Firm—Bert J. Lewen

[57] ABSTRACT

This invention concerns the preparation of oxirane compounds by the vapor phase cracking of hydroxyesters in the presence of a basic material. Specifically, it has been discovered that the aforesaid reaction may be carried out without the prior separation of vicinal glycols, vicinal diesters or both. This is particularly advantageous because vicinal hydroxyesters are frequently formed in combination with these latter materials and the separation thereof is most difficult. Preferably, mixtures of the hydroxyesters, glycols and diesters are first hydrolyzed or esterified in order to increase the hydroxyester content.

7 Claims, No Drawings

CRACKING OF MIXTURES CONTAINING HYDROXYESTERS

DESCRIPTION OF THE INVENTION

This invention relates to a new and improved process for preparing oxiranes. More specifically, the instant invention relates to the preparation of oxiranes from hydroxyesters by vapor phase cracking in the presence of a basic material as more fully described in U.S. patent application Ser. No. 44,836 filed Feb. 22, 1974 and abandoned, now published as Belgian Patent No. 812,109.

The hydroxyester feed for the aforesaid cracking process is most generally found in combination with other materials, namely, vicinal diesters and glycols. For example, hydroxyesters may be obtained from the oxidation of an olefinically unsaturated compound with molecular oxygen in a carboxylic acid medium in the presence of a catalyst. Such oxidation processes are described in Kurishiki Rayon's British Patent No. 1,124,862; Celanese Corporation's U.S. Pat. Nos. 3,479,395 and 3,637,515; and Halcon International's U.S. Pat. Nos. 3,668,239, 3,770,813, 3,715,388, 3,715,389, 3,743,672, 3,778,468 and 3,789,065. While these processes produce varying amounts of the vicinal hydroxyesters, alkylene glycol diesters and glycols are also formed.

The vicinal hydroxyesters may also be obtained by the esterification of vicinal glycols. Again, the products which are formed include equilibrium concentrations of unreacted vicinal glycols and vicinal diesters.

Another source of feedstock for the reaction is the unreacted materials from the cracking process itself. After the separation of the desired oxirane compounds, there remain admixtures of alkylene glycol monoesters, alkylene glycol diesters and alkylene glycols, with the diester as the preponderant constituent.

Prior to applicant's discovery, as more fully described herein, it was believed that in order to successfully practice the cracking process, it was necessary to separate the vicinal glycols and diesters. The main reason for this expectation was that vicinal glycols and diesters in their pure state, when contacted with the basic oxirane-forming catalyst, decompose nonselectively to form unwanted products and would therefore lower the selectivity of the overall reaction.

In accordance with this invention, however, it has been discovered that the aforesaid mixtures of the hydroxyesters, glycols and/or diesters may be passed directly to the cracking step without lessening the efficiency of the conversion of the hydroxyester to the oxirane. This is a particular advantage because the separation of the hydroxyesters, diesters and glycols proved difficult because of their similar solubility characteristics and very close boiling points. For example, ethylene glycol, ethylene hydroxyacetate and ethylene diacetate have boiling points of 198°, 190° and 190° C., respectively, and propylene glycol, propylene hydroxyacetate and propylene diacetate of 188.2°, 185° and 186° C., respectively.

Though the mixture could be countercurrently extracted with xylenes using water as a counter solvent to separate the diacetate (which enters the xylene) from the glycol and hydroxyester, both solvents would then have to be distilled from the products, incurring a high energy cost. The glycol could thereafter be removed from the hydroxyester by distillation as a low boiling azeotrope by addition of an azeotrope-forming compound as described in U.S. Pat. No. 3,809,724. This step also requires a large expenditure of energy. Similarly, the glycol and hydroxyester could also be separated by extraction.

When the mixture of hydroxyester, glycol and diester contains a preponderance of either of the latter two components, it is a preferred embodiment of this invention to treat such mixture to effect 20 to 80% esterification, preferably from 30 to 70%. Where the diester is the preponderant constituent, the treatment selected is hydrolysis, while when the glycol is the predominant constituent, esterification is used. This embodiment is particularly important since the cracking of mixtures containing lesser amounts of the hydroxyester gives such low conversions per pass that the processes cannot be practically employed for forming oxiranes. The percent esterification as referred to herein may be better understood by recognizing that the glycol per se is completely unesterified, the hydroxyester is 50% esterified and the diester is 100% esterified. From a statistical point of view, if the percent esterification is in the broad range set forth above, namely, from 20 to 80%, the equilibrium mixture will contain a mole fraction of the hydroxyester of at least 0.32, while in the case of the preferred range, namely, from 30 to 70%, the mole fraction of the monoester is at least 0.42.

The esterification and hydrolysis may both be either acid- or base-catalyzed, as is well known to those skilled in the art. Typical acid catalysts are sulfuric acid, phosphoric acid, acid ion exchange resins and most preferably the acid of the ester of the hydroxyester reactant. Typical base catalysts are alkali metal and alkaline earth metal carboxylates. Catalyst concentrations of from 0.05 to 0.5 mole equivalents are generally used to achieve the desired reaction rate. Catalyst addition is most important at temperatures below 180° C.; otherwise the reaction is sluggish.

The use of the carboxylic acid is particularly preferred because it does not require the addition of another component to the system. Temperatures for the hydrolysis and esterification are from 80° to 250° C., preferably from 130° to 220° C. Lower temperatures slow the rate of this reaction, while higher temperatures lead to product decomposition. The time for the mixture to reach equilibrium depends on the catalyst concentration, temperature, and the starting mixture. Normally, times from 0.5 to 5 hours are sufficient.

Thereafter, the equilibrium mixture from the hydrolysis or esterification, as the case may be, may be passed directly to the cracking step. The reaction products from the cracking may be separated by distillation and the carboxylic acid product, unreacted hydroxyester, diesters and glycol, along with diluent, may be recycled to hydrolysis or esterification, whichever, is appropriate. After the separation of the carboxylic acid (to 1 wt. % or less), the hydrolysis or esterification effluent may be recycled.

It will be understood that while the aforesaid invention describes the treatment of materials obtained from an olefinic oxidation step and from the recycle of the cracking step, such materials may be obtained from other sources. Additionally, as a practical matter, it may well be that the cracker receives material from both of the aforesaid sources with either one or both being hydrolyzed before being fed to the cracker.

While the cracking step is fully described in Belgian Patent No. 812,109, the cracking step may be outlined as follows: Preferably, a saturated solution or a 0.1 molar aqueous solution (whichever has less solute) of the basic material has a pH of from 8 to 13. It is believed that during the reaction an alkaline carboxylate forms which is continually regenerated in situ. The basic material which may be added is preferably an alkali or alkaline earth metal borate, phosphate, oxide, carbonate, aluminate or silicate. These materials may be unsupported or supported on a neutral or basic carrier such as alpha-alumina, silicon carbide, silicon silicate, zirconium silicate and aluminum silicate.

The hydroxyester containing the glycol, diester or both, may be fed to the reaction zone without more, or, if desired, diluted with a carrier gas. The carrier gas may be a liquid at room temperature, such as benzene, toluene, xylene, pseudocumene or water or a non-condensable carrier gas such as nitrogen, helium or carbon dioxide. When a carrier gas is used, the hydroxyesters are from about 10 to 75% by weight, preferably from 25 to 60%, of the total feed.

The reaction temperature must be sufficient to maintain the hydroxyester in the vapor phase under reaction conditions. Suitable temperature ranges vary depending on the particular hydroxyester, the presence of the carrier gas and the system pressure. Generally, the deacyloxylation or cracking of the hydroxyester proceeds at a temperature of from about 250° to about 600° C., preferably from 250° to 450° C. and most desirably from 350° to 425° C.

Pressures may be up to 400 psia and vacuum down to 0.1 psia. The partial pressure of the hydroxyester should generally not exceed 100 psia and for ease of operation atmospheric pressure is often preferred. Surprisingly, however, it has been found that reduced pressure operation results in higher conversions without loss of selectivity. Therefore, it is preferred that the partial pressure of the hydroxyester be from 1 to 15 psia, most desirably from 2 to 8 psia.

For optimum conversion, feed rates from 0.5 to 1000 moles of hydroxyester per mole of basic material per hour may be used. Preferably, the feed rate is from 5 to 250 moles per mole per hour and most desirably from 10 to 100 moles per mole per hour.

The deacyloxylation produces the corresponding oxirane and an equimolar amount of the carboxylic acid as shown in the following equation:

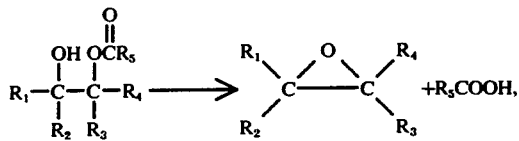

wherein $R_1$, $R_2$, $R_3$, $R_4$ and $R_5$ may be hydrogen; alkyl, alkenyl or alkynyl up to 16 carbon atoms; an aryl group, such as phenyl or naphthyl; cyano:

where $R_6$ is hydrogen, alkyl, alkoxy, carbomethoxy, or carboacyl. The aforesaid hydrocarbon groups may be substituted with electron withdrawing groups, e.g., one or more halo, nitro, sulfo or cyano groups. Additionally, the aryl group may be substituted with alkyl groups having 1 to 4 carbon atoms; and the alkyl groups, with a phenyl group. Preferably, at least two of the aforesaid R groups are hydrogen, and the remaining ones hydrogen, methyl, ethyl, propyl, butyl, or phenyl. $R_1$ and $R_4$ may be joined as common members of a cyclic compound having from 4 to 16 carbon atoms, such as cyclobutane, cyclohexane and cyclododecane. $R_5$ is preferably alkyl having from 1 to 3 carbon atoms with or without electron withdrawing groups.

Examples of suitable hydrocarbon radicals substituted with electron withdrawing groups are: trichloromethyl, tribromomethyl, trifluoromethyl, chlorodifluoromethyl, fluorodichloromethyl, bromodichloromethyl, bromodifluoromethyl, cyanomethyl, dichloroethyl, nitro methyl, iodomethyl, sulfomethyl, difluoropropyl, nitro phenyl, fluorophenyl, 2,4-difluorophenyl, 2,4-dibromophenyl, 2,4,6-trichlorophenyl, p-chlorophenyl, p-bromophenyl, p-sulfophenyl, p- and m cyanophenyl, iodophenyl, chloro- and fluoronaphthyl, dinitronaphthyl, chloro- and bromocyclohexyl, chloronorbornyl and bromodecalin. $R_1$ and $R_5$ may also be acetyl, carboxyl, carbomethoxy, carboethoxy, aldehydic and carboacetyl. Vinylogous acid and ester groups may be employed, as for example the maleic acid half-ester of isopropanol.

Illustrative examples of the hydroxyesters suitable as starting material in this invention are those derived from such olefins as ethylene, propylene, butylenes, pentenes, styrene and alpha-methylstyrene. Also suitable are substituted olefins such as allyl alcohol and allyl chlorides. Moreover, non-conjugated diolefins, such as 1,4-hexadiene, are suitable for this invention. In this instance, the product would be the corresponding diepoxide, whereas with such substituted olefins as allyl chloride, the product would be epichlorohydrin.

The ester is most preferably of acetic acid because of its ready availability. Other acids which may be used include propionic acid, butyric acid, benzoic acid, chloroacetic acid, trichloroacetic and phenylacetic acid.

The oxirane compounds which can be prepared by practicing the instant invention include: ethylene oxide; propylene oxide; 2,3-dimethyloxirane: 2,2-dimethyloxirane; phenyloxirane; 2-methyl-2-phenyloxirane; 2-n-butyloxirane; cyclohexene oxide; cyclopentene oxide; stilbene oxide; cyclododecene oxide; cyclooctene oxide; 2-cyclohexyloxirane; norbornene oxide; n- and isodecyloxirane; n- and isoheptyloxirane; and n- and isohexadecyloxirane.

To illustrate the invention more fully, attention is directed to the following examples:

EXAMPLE 1

A 4 inch stainless steel reactor having a volume of 40 cc was charged with 32 g of catalyst. The catalyst was 8.65 weight percent potassium silicate on 8 to 12 mesh alundum. Relatively pure propylene glycol monoacetate was fed to this system and for comparison purposes feeds containing significant quantities of propylene glycol or propylene glycol diacetate were also run.

The conditions of the test are outlined in the table below.

| | 1 | 2 | 3 |
|---|---|---|---|
| Component, Mole % | Feed Compositions | | |
| Propylene glycol monoacetate | 50.6 | 36.5 | 38.9 |
| Propylene glycol | 1.5 | 25.1 | 4.2 |

|  | -continued | | |
|---|---|---|---|
| diacetate | | | |
| Propylene glycol | 6.5 | 11.4 | 29.7 |
| H₂O | 41.4 | 27.0 | 27.2 |
| Conditions | | Conditions | |
| Temperature, °C. | 400 | 400 | 400 |
| Total pressure, mm Hg | 100 | 160 | 160 |
| Propylene glycol monoacetate, partial pressure, mm Hg | 51 | 58 | 62 |
| Contact time (empty tube basis), seconds | .92 | .84 | 1.07 |
| Results | | Results | |
| Propylene glycol monoacetate conversion, % | 36.6 | 37.7 | 31.8 |
| Selectivity to propylene oxide, % | 87.8 | 93.7 | 87.8 |

This illustrates that there was no detrimental effect on the results, especially selectivity, when large amounts of diacetate and glycol are included in the feed.

Comparative Example A

In two separate runs, pure propylene glycol and pure propylene glycol diacetate were pumped through a vaporizer and passed over a catalyst composed of 10% by weight sodium borate supported on alpha-aluminum at one atmosphere pressure under the conditions shown below.

| | Feed | |
|---|---|---|
| | 100 Wt. % Propylene Glycol | 100 Wt. % Propylene Glycol Diacetate |
| Flow, cc/hr | 58 | 56 |
| Temperature, °C. | 360 | 369 |
| Catalyst Wt., gms. | 10.9 | 15.5 |
| Conversion, % | 4.0 | 3.0 |
| Selectivity | | |
| Propylene Oxide | 26 | 17 |
| Propionaldehyde | 11 | 52 |
| Acetone | 13 | 31 |
| Allyl Alcohol | 41 | — |
| Other | 9 | — |

As will be apparent from the above data, extremely large amounts of propionaldehyde, acetone and allyl alcohol were formed when the pure components were reacted. This is in sharp contrast to the results shown in Example 1, where little non-selective decomposition is evident.

EXAMPLE 2

One hundred grams of propylene glycol diacetate was mixed with 200 grams of water and heated to 185° C. The system pressure rose to 80 psig. After five hours the system was cooled and the acetic acid and water distilled overhead. The product mixture was 55 wt. % propylene glycol monoacetate, 33% diacetate and 12% propylene glycol.

This mixture was then fed at a rate of 1.3 grams per minute to a reactor containing a catalyst composed of 40 grams of 11.8 wt. % K₂Si₂O₅ on 8-12 mesh alundum operating at 400° C. and 250 mm Hg pressure. Thirty-two percent of the propylene glycol monoacetate reacted to yield propylene oxide, propionaldehyde and acetone in molar selectivities of 85%, 10% and 5%, respectively.

EXAMPLE 3

One hundred grams of propylene glycol was charged to a vessel containing 150 grams of acetic and 0.25 gram of sulfuric acid. The mixture was heated to 200° C. at a pressure of about 140 psig for two hours. After cooling the acetic acid and water were distilled overhead and then the mixed glycol esters were vaporized and collected. The product mixture was 30 wt. % propylene glycol diacetate, 50% monoacetate and 20% glycol.

This mixture was then fed at a rate of 2.0 grams per minute to a reactor containing a catalyst composed of 80 grams of 15 wt. % sodium silicate on carborundum operating at 410° C. and 300 mm Hg. Forty-two percent of the monoacetate was converted to propylene oxide, propionaldehyde and glycol in molar selectivities of 78%, 18% and 8%, respectively. Conversions of the diacetate and glycol were less than 1%.

EXAMPLE 4

A feed composed of 41 wt. % propylene glycol monoacetate, 52 wt. % propylene glycol diacetate, 2 wt. % propylene glycol and 4 wt. % water was fed to a multi-bed cracking reactor with inter-stage reheat. The catalyst was 15 wt. % potassium silicate on ⅛ inch carborundum. The reaction temperature varied from 425 to 400° C. over each bed and the exit pressure was 5.6 psia. Vapor residence time was one second. Forty percent of the monoacetate reacted to form propylene oxide, propionaldehyde and acetone in 85%, 10%, and 5% molar selectivities, respectively.

The reaction products were cooled, condensed and the vapors compressed to atmospheric pressure to condense the cracked products. After collection of all the reaction liquids the propylene oxide, propionaldehyde and acetone were removed by distillation for further purification. The column bottoms were composed of:

| | |
|---|---|
| Acetic Acid | 9.2 wt. % |
| Propylene Glycol Monoacetate | 27.2 wt. % |
| Propylene Glycol Diacetate | 58.1 wt. % |
| Propylene Glycol | 1.0 wt. % |
| H₂O | 4.5 wt. % |
| | 100.0 wt. % |

The bottoms were pumped to 250 psig and heated to 220° C. for one hour to re-equilibrate the mixture. The product concentrations after this period were:

| | |
|---|---|
| Acetic Acid | 13.8 wt. % |
| Propylene Glycol Monoacetate | 36.2 wt. % |
| Propylene Glycol Diacetate | 45.8 wt. % |
| Propylene Glycol | 1.0 wt. % |
| H₂O | 3.2 wt. % |
| | 100.0 wt. % |

The acetic acid and water were distilled from this mixture and the remaining material joined with a fresh feed, made from an olefin acetoxylation process, composed of 35 wt. % propylene glycol monoacetate, 47 wt. % diacetate and 18% water to reform the starting feedstock. The combined materials containing 41 wt. % propylene glycol monoacetate, 52 wt. % diacetate and 2 wt. % glycol were feed to cracking reactor described above. The conversion and product distribution were substantially the same.

EXAMPLE 5

A feed mixture containing 40 wt. % ethylene glycol monoacetate, 45% diacetate and 15% water was fed to a cracking reactor at the rate of 0.7 grams per minute. The reactor contained 40 grams of 8 wt. % sodium acetate on silica and was at 410° C. and 100 mm Hg. The monoacetate conversion was 45% and formed ethylene oxide and acetaldehyde in molar selectivities of 65% and 35%, respectively. Negligible reaction of the diacetate or glycol occurred.

We claim:

1. In a process for preparing an oxirane compound from the alkylene glycol monoester of an olefin and a carboxylic acid, wherein the olefin is ethylene, propylene, a butylene, a pentene, styrene, or alpha methylstyrene, and the carboxylic acid is acetic, propionic, or butyric, and wherein said alkylene glycol monoester is subjected to a cracking step in the vapor phase in the presence of a basic material, the improvement of: hydrolyzing a mixture containing a preponderance of alkylene glycol diester or esterifying a mixture containing a preponderance of alkylene glycol, thereby obtaining an effluent, said hydrolysis or esterification being performed so as to maximize the alkylene glycol monoester in such mixture and to achieve a mole fraction concentration thereof of at least 0.32 (based on the total amount of alkylene glycol diester, alkylene glycol monoester and alkylene glycol); and thereafter passing the effluent to the cracking step, without the prior separation of the alkylene glycol diester or the alkylene glycol from the alkylene glycol monoester.

2. The process of claim 1 wherein the mole fraction concentration of the alkylene glycol monoester in the effluent is at least 0.42 (based on the total amount of alkylene glycol diester, alkylene glycol monoester and alkylene glycol).

3. A process for preparing an oxirane compound from the alkylene glycol monoester of an olefin and a carboxylic acid, wherein the olefin is ethylene, propylene, a butylene, a pentene, styrene, or alpha-methylstyrene, and the carboxylic acid is acetic, propionic, or butyric, which comprises: esterifying a mixture containing a preponderance of alkylene glycol with a carboxylic acid so as to maximize the alkylene glycol monoester and to achieve a mole fraction concentration thereof of at least 0.32 (based on the total amount of alkylene glycol diester, alkylene glycol monoester and alkylene glycol); separating the unreacted carboxylic acid; and thereafter passing the esterification effluent, without the separation of unreacted alkylene glycol, to a cracking step, wherein the alkylene glycol monoester is cracked in the vapor phase in the presence of a basic material.

4. A process for preparing an oxirane compound from the alkylene glycol monoester of an olefin and a carboxylic acid, wherein the olefin is ethylene, propylene, a butylene, a pentene, styrene, or alphamethylstyrene, and the carboxylic acid is acetic, propionic, or butyric, which comprises: hydrolyzing a mixture containing a preponderance of alkylene glycol diester so as to maximize the alkylene glycol monoester and to achieve a mole fraction concentration thereof of at least 0.32 (based on the total amount of alkylene glycol diester, alkylene glycol monoester and alkylene glycol) and to form the carboxylic acid; separating the carboxylic acid; and thereafter passing the hydrolyzed mixture, without the separation of the unreacted alkylene glycol diester, to a cracking step, wherein the alkylene glycol monoester is cracked in the vapor phase in the presence of a basic material to form the oxirane compound.

5. In a process for preparing an oxirane compound from an olefin wherein the olefin is initially oxidized with molecular oxygen in the presence of a carboxylic acid to form an admixture of the alkylene glycol monoester and the alkylene glycol diester, wherein the olefin is ethylene, propylene, a butylene, a pentene, styrene, or alpha-methylstyrene, and the carboxylic acid is acetic, propionic, or butyric, and wherein the alkylene glycol monoester is cracked in the vapor phase in the presence of a basic material, the improvement of: hydrolyzing the admixture to maximize the alkylene glycol monoester and to achieve a mole fraction concentration thereof of at least 0.32 (based on the total amount of alkylene glycol diester, alkylene glycol monoester and alkylene glycol); separating at least some of the water and the carboxylic acid from the hydrolysis effluent; and passing the remainder of the admixture, without the separation of the alkylene glycol diester, to said cracking step.

6. In a proces for the vapor phase cracking of an alkylene glycol monoester derived from oxygen, an olefin, and a carboxylic acid, wherein the olefin is ethylene, propylene, a butylene, a pentene, styrene, or alpha-methylstyrene, and the carboxylic acid is acetic, propionic, or butyric, in the presence of a basic material wherein the reaction effluent contains the oxirane product, unreacted alkylene glycol monoester, alkylene glycol diester and alkylene glycol and wherein the oxirane product is separated from the glycol and the aforesaid esters, the improvement of: hydrolyzing the remaining alkylene glycol and esters to maximize the alkylene glycol monoester and to achieve a mole fraction concentration thereof of at least 0.32 (based on the total amount of alkylene glycol diester, alkylene glycol monoester and alkylene glycol); separating at least part of the water and the carboxylic acid; and recycling said mixture, without the separation of the alkylene glycol or alkylene glycol diester, to said cracking step.

7. The process of claim 1 wherein the alkylene glycol monoester is the hydroxyacetate of ethylene, propylene or butylene.

* * * * *